United States Patent [19]

Francard

[11] Patent Number: 4,988,948

[45] Date of Patent: Jan. 29, 1991

[54] METHOD FOR THE AUTOMATIC LINE CALIBRATION OF A SENSOR FOR MEASURING THE CONCENTRATION OF A LIQUID PHASE DISSOLVED ELECTROCHEMICAL SUBSTANCE

[75] Inventor: Jean-Louis Francard, Magny les Hameaux, France

[73] Assignee: Technicatome Societe Technique pour l'Energie Atomique, France

[21] Appl. No.: 366,784

[22] Filed: Jun. 15, 1989

[30] Foreign Application Priority Data

Jun. 15, 1988 [FR] France ............................ 88 08000

[51] Int. Cl.$^5$ ...................... G01N 27/27; G01N 27/31
[52] U.S. Cl. ................................ 324/444; 324/438; 324/439; 324/450; 204/153.13
[58] Field of Search ............... 324/438, 439, 441, 444, 324/450; 73/1 G; 204/1 T, 400, 405

[56] References Cited

U.S. PATENT DOCUMENTS 4,713,618 12/1987 Carlson et al. ............... 423/450 X

FOREIGN PATENT DOCUMENTS 0218469 4/1987 European Pat. Off. .

OTHER PUBLICATIONS

Patent Abstracts of Japan, vol. 6, No. 248, Dec. 7, 1982;

and JP-A-57 147 047 (Olympus Kogaku Kogyo K.K.) 10-09-82.

Primary Examiner—Reinhard J. Eisenzopf
Assistant Examiner—Jack B. Harvey
Attorney, Agent, or Firm—Nutter, McClennen & Fish

[57] ABSTRACT

A method for the automatic line calibration of an electrochemical sensor for measuring the concentration of a liquid phase dissolved electrochemical substance flowing into a pipe and is characterized by the following stages: upstream of the electrochemical sensor, a generator is placed on the pipe, the generator being suitable for delivering standard quantities of the substance; between the generator and the electrochemical sensor, a delay line (3) is placed on the flow with a given volume of this liquid. By way of the generator, successively injected into the liquid pipe are two bursts of known quantities of the electrochemical substance corresponding to the concentration $C_1$ and $C_2$ in the liquid flow. From the indications of the electrochemical sensor (4), the delay time introduced by the delay time is determined. The meter constant K of the substance concentration as indicated by the sensor is calculated by producing the ratio of the difference of the indications of the sensor to the difference of the concentrations $C_2-C_1$.

5 Claims, 3 Drawing Sheets

METHOD FOR THE AUTOMATIC LINE CALIBRATION OF A SENSOR FOR MEASURING THE CONCENTRATION OF A LIQUID PHASE DISSOLVED ELECTROCHEMICAL SUBSTANCE

FIELD OF THE INVENTION

The present invention concerns the automatic line measurement of the concentration of a electrochemical substance dissolved in a liquid flowing in a pipe.

BACKGROUND OF THE INVENTION

More precisely, the continuous and automatic measurement of the concentration of such an electrochemical substance is embodied in a known way with the aid of a galvanic cell-type electrochemical sensor, which output delivers an electric intensity proportional to the concentration of the chemical substance dissolved in the liquid with which the sensor is in contact, through a semipermeable membrane, for example.

Unfortunately, and this is a phenomenon well-recognised by experts, such concentration sensors present two major drawbacks which impair their reliability:

The first drawback derives from the instability of the meter constant K of such a device between the electric intensity i it delivers and the concentration of the substance being observed. This constant effectively varies according to the time and temperature, which requires a continuous recalibration of the device so as to have perfectly reliable measurements.

Moreover, another drawback of this type of device results from the fact that, by virtue of its actual principle, it undergoes a certain amount of wear of its electrodes which leads it to a final state in which its indication is continuously nil, regardless of the concentration of the chemical substance monitored. This property constitutes a major drawback, as a nil indication of the sensor clearly constitutes an uncertainty due to the fact that it may be caused by both the absence of the substance sought-for and the definitive wear of the sensor.

In order to overcome this kind of difficulty, it is possible to periodically recalculate the instantaneous value of the meter constant K of the sensor by using the dosed additions method. This consists of injecting upstream in the pipe passed through by the liquid to be monitored known quantities of the chemical substance to be monitored and of deducing from this the instantaneous value of the meter constant K by studying the behavior of the response obtained at the level of the electrochemical sensor. However, such a method requires the use of a flowmeter, as the injector used, generally an electrolytic Faraday cell, making it possible to know the quantity of the substance injected but not its concentration. In order to know its concentration, it is necessary to use a flowmeter, which is a less reliable device having, in particular, heating systems or mobile elements and bearings, such as turbine bearings; such a device is also expensive, it alone representing more than 10% of the total cost of an automatic line concentration measuring installation.

Because of the above-mentioned reasons, there currently exists no reliable method for line measuring the concentration of a dissolved chemical substance which allows for the automatic calibration of the electrochemical sensor at periodic intervals.

SUMMARY OF THE INVENTION

The precise object of the present invention is to provide a method for the automatic line calibration of such an electrochemical sensor, said method resolving the aforesaid problem by means of simple, reliable and effective means.

This method for the automatic line calibration of the concentration of a dissolved liquid phase electrochemical substance flowing in a pipe is characterized by the following stages:

upstream of the electrochemical sensor, a generator is placed on the pipe passed through by the liquid flow to be monitored, said generator being suitable for delivering in this flow standard quantities of the substance whose concentration is desired to be measured;

between the preceding generator and the electrochemical sensor, a delay line is placed on this same flow with a given volume of this liquid;

by means of the generator, injected successively into the liquid pipe are two bursts of known quantities of the electrochemical substance corresponding to the concentrations $C_1$ and $C_2$ in the liquid flow;

from the indications of the electrochemical sensor, the delay time introduced by the delay line between the generator and the sensor for each said burst is determined and of then deducing from this the flow Q of the liquid;

the meter constant K of the substance concentration as indicated by the sensor is calculated by producing the ratio of the difference of the indications of the sensor to the difference of the concentrations $C_2-C_1$.

As can be seen here, the calibration method of the present invention, which functions with an electrochemical sensor of the galvanic type able to drift from its meter constant, makes it possible to avoid using a flowmeter to measure the flow Q of the liquid in the pipe. To this effect, the flowmeter is replaced by the presence of a "hydraulic" delay line, in other words a pipe section added between the generator and the sensor, combined with the injection of two successive concentrations $C_1$ and $C_2$ of known values of the electrochemical substance to be monitored into the liquid flow. A knowledge of the flow Q is necessary so as to determine the concentration corresponding to the masses injected into each of the two bursts of the electrochemical substance.

Of course in practice, the various stages of the method of the invention occur via the order of a microprocessor which controls the various sequences of this and periodically carries out a calculation of the meter constant K or at moments selected by the user.

The calibration method of the invention uses in an original way the method known as the "dosed additions" method, said calibration method firstly starting by verifying, prior to injection by means of the generator of two bursts of the electrochemical substance to be monitored, that the level of this substance in the flow to be monitored is close to its normal value. If this has not been the case, the quantities thus added by the generator could easily pass unnoticed in the presence, for example, of an abnormally high concentration in the pipe at the moment the sequences are triggered which shall result in the actual determination of the constant K and in a recalibration of the device.

According to the invention, the hydraulic delay line located between the generator and the sensor is constituted by a passive extension piece of the pipe, for example in the form of a helicoidal-shaped stainless steel tube whose internal volume is close to 100 cm$^3$.

According to a more precise characteristic of the automatic calibration method of the invention, the generator is a Faraday cell with two electrodes bathing in the liquid flow to be monitored and suitable for freeing into this liquid concentrations of the electrochemical substance with the form $C = C_f I/Q$, a formula in which $C_f$ is the corrected Faraday constant of the efficiency of electrolysis, I the intensity of the current injected into the cell and Q the flow of the liquid in the pipe where it flows; the electrochemical sensor for measuring the concentration of the electrochemical substance is a galvanic membrane cell in contact with the liquid to be monitored, having two electrodes bathing in a bath solution and delivering a current $i = KC$, K being the meter constant of the device whose stability is verified, and C the value of the concentration of the electrochemical substance in the liquid flow to be monitored.

An experimental determination is made of the delay T introduced by the delay line between the period for injecting a substance by the cell and the detection of the latter by the sensor according to the flow Q of the liquid in the pipe, the function $T = f(1/Q)$ being linear by definition.

Into the Faraday cell, two levels of currents $I_1$ and $I_2$ are successively injected, each freeing in the pipe the additional electrochemical substance concentrations $C_1$ and $C_2$ so that $C_1 = C_f I_1/Q$ and $C_2 = C_f I_2/Q$.

The stopping instants $T_A$ and $T_C$ of these levels of current $I_1$ and $I_2$ are respectively marked, the respective initial decline instants $T_B$ and $T_D$ of the current i corresponding to the output of the galvanic cell, the values $i_1$ and $i_2$ of i also corresponding to these same instants $T_B$ and $T_D$.

The flowrate Q in the pipe is calculated at the moment of the experiment by carrying forward onto the straight line $T = f(1/Q)$ the mean value:

$$\frac{(T_B - T_A) + (T_D - T_C)}{2}$$

From this, the current value K of the meter constant of the cell is deduced via the formula:

$$K = \frac{Q}{C_f} \times \frac{i_2 - i_1}{I_2 - I_1}$$

According to the invention, it can be seen that, in order to measure the delay made in the outflow of the liquid by the delay line, one preferably chooses to introduce between the generator and the sensor instants with rising up of the intensities i at the output of the galvanic cell, said intensities being particularly well-defined and easier to mark than the initial decline instants of this same current i. In order to calculate the flowrate of the liquid phase in the pipe at the time of calibration with the aid of the function $T = f(1/Q)$, which is linear and is determined experimentally, recourse is made, so as to improve accuracy of the measurement, to the average or mean of the delays established from each of the two current levels $I_1$ and $I_2$ addressed to the Faraday cell. According to the invention, it is clearly the use of these two injections, corresponding to known and controlled concentrations of the electrochemical substance to be monitored in the pipe where the liquid phase to be monitored flows, that makes it possible to avoid the use of a flowmeter so as to pass quantities of the substance freed in the Faraday cell at the concentration they represent once injected into the liquid flow of the pipe.

According to a preferred mode for implementing the method of the invention, the electrochemical substance to be monitored is a solution of oxygen in running water, the Faraday cell being cylindrically-shaped with concentric electrodes made of stainless steel and the galvanic membrane cell having electrodes respectively made of lead and silver.

Finally, the method of the invention can generally be used for monitoring the concentration of any electrochemical substance dissolved in running water since it is able to provoke typical electrochemical reactions. By way of example, the present invention can be properly applied to a method for dosing the concentration of chlorides in water in which the generator of ions $Cl^-$ in the running water is an electrolysis cell having its electrodes made of Cu and an Ag-AgCl alloy, the electrochemical sensor having an electrode specific for measuring the concentration of the chlorine.

BRIEF DESCRIPTION OF THE DRAWINGS

The invention shall be more readily understood from a reading of the following description, given by way of illustration and being in no way restrictive, and with reference to FIGS. 1 to 6 in which.

DETAILED DESCRIPTION OF THE PREFERRED EMBODIMENTS

Figure 1:
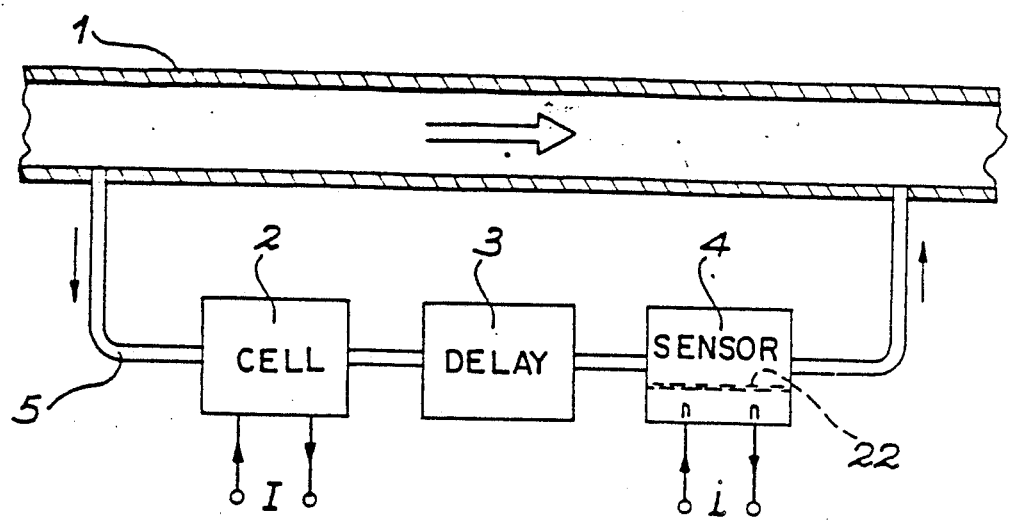
FIG. 1 represents the skeleton diagram of the apparatus required for implementing the method of the invention.

In the example shown on FIG. 1, diagrammatized at 1 is a pipe passed through by a liquid flow in which is dissolved an electrochemical substance whose concentration is desired to be continuously measured.

The apparatus required to implement the automatic line calibration method of the invention mainly comprises a generator or cell 2 for this electrochemical substance, a "hydraulic" delay line 3 and a sensor 4. In the example of FIG. 1, the generator or cell 2, delay line 3 and the sensor 4 are series-connected on a branch circuit connection 5 with flow Q of the liquid passing through the pipe 1, but it is quite clear that, depending on the cases of application, it is also possible to series-connect everything on the pipe 1 itself.

The generator 2 is an electrochemical type generator, most often being a Faraday cell, suitable for discharging into the pipe 5 controlled quantities of the electrochemical substance whose concentration is monitored and being under the effect of the control of a current I injected into it. The "hydraulic" delay line 3 is a passive pipe with a certain length and merely intended to artificially elongate the path of the liquid phase in the branch circuit connection 5 between the output of the generator 2 and the input of the sensor 4. The sensor 4 is a galvanic cell comprising two electrodes, one being an anode and one a cathode being immersed in an electrolyte or bath solution separated by a semipermeable membrane 22 from the liquid phase which flows into the branch circuit connection 5. The electrochemical substance, whose concentration is to be monitored, must be able to firstly traverse this membrane and secondly, having thus penetrated the electrolyte, to provoke electrochemical reactions with one of the electrodes so as to modify the electrochemical equilibrium of the cell and have emitted to it a current of electrons expressed externally by a current i accessible to the measurement. Such galvanic cells are familiar to experts in this field and it is known that their current response i is proportional to the concentration of the electrochemical substance carried by the liquid with which it is in contact. In other words, this sensor 4 functions as an electric battery which externally delivers a current $i = KC$, C being the value of the concentration of the monitored electrochemical substance in the liquid flow Q of the branch circuit connection 5 and K being the meter constant of the sensor 4.

Unfortunately, the constant K is unstable and evolves over a period of time under the effect of firstly variations of temperature and secondly the state of wear of the electrodes of the sensor 4. This is precisely why it is necessary to resort to a calibration method such as the method of the invention if it is desired to automatically obtain reliable results avoiding variations of the constant K.

In order to implement this method, successively delivered into the pipe 5 by means of the generator are two bursts of the electrochemical substance to be monitored at known concentrations able to be marked. Then a measurement is made of the variations of the current of i consecutive to the arrival, with the delay introduced by the line 3, of said two bursts on the sensor 4 and from this, as explained with the aid of FIGS. 3 and 4 following, the instantaneous value of the constant K is deduced, which thus makes it possible to gain access to the real value of the concentration of the monitored electrochemical substance.

Figure 2:
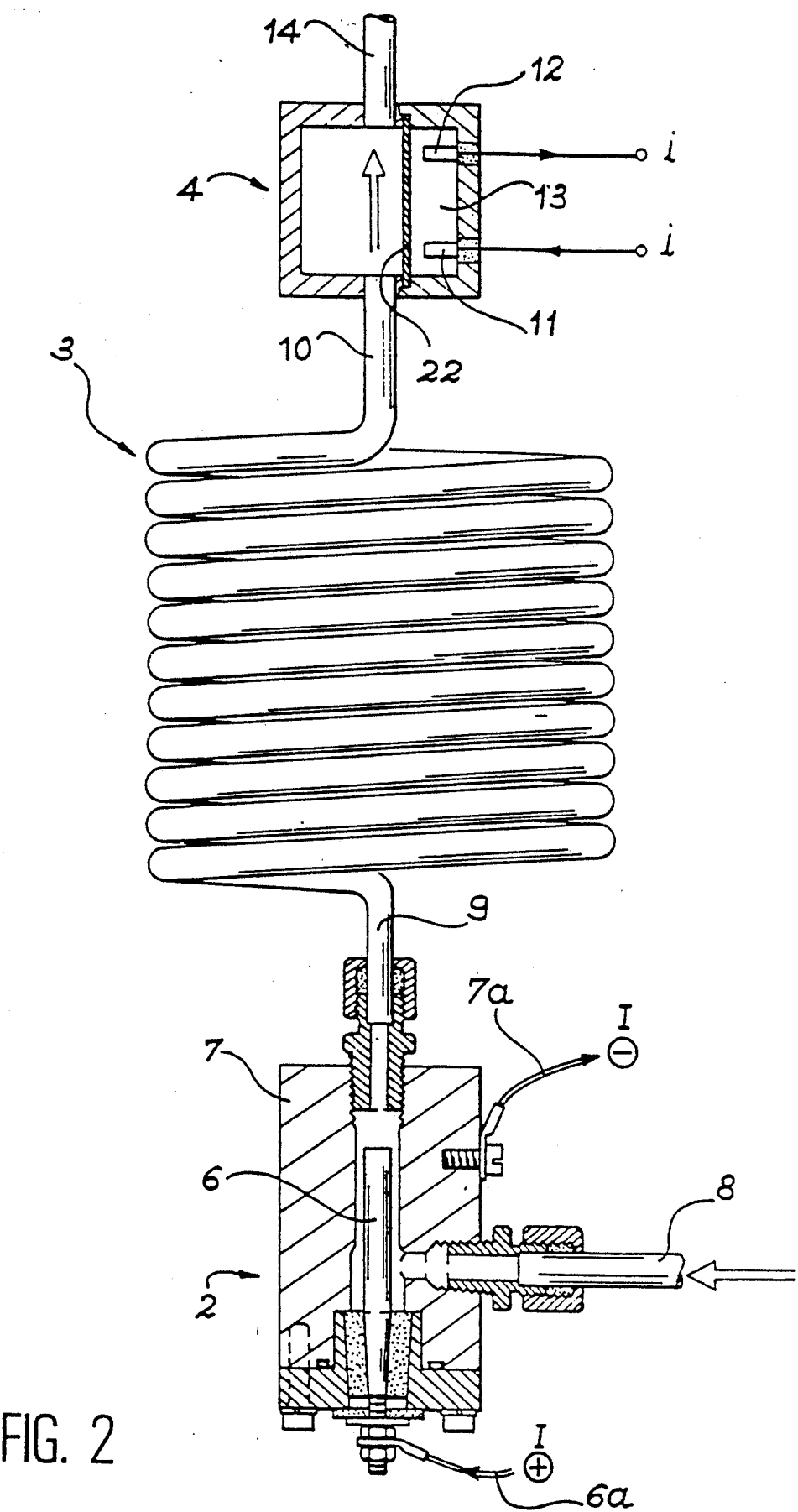
FIG. 2 represents a mode for practically implementing this apparatus.

FIG. 2 shows in detail a practical embodiment of the apparatus of FIG. 1 which shows the generator 2, the delay line 3 and the sensor 4. The generator 2 is a cylindrically-shaped Faraday cell possessing two concentric electrodes 6 and 7. The central electrode 6 used as an anode is made of pure nickel so as to limit the effects of corrosion. The electric current with intensity I is injected to the cell by the conductors 6a for the central anode 6 and 7a for the cathode 7. The input of the liquid phase 8 receives the flow Q of the branch circuit connection 5 of FIG. 1, said flow penetrating the pipe 9 of the generator 2. This liquid flow then penetrates the hydraulic delay line 3, which is merely a passive pipe made up of a stainless steel tube helicoidally wound like a pipe coil, as can be seen on the figure and having, in the example described, an internal volume approaching 100 cm³. The liquid which flows into the installation then penetrates via the pipe 10 into the sensor 4 whose active part comprises the two electrodes 11 and 12 bathing in the electrolyte 13. This electrolyte 13 is separated by a membrane 22 from the liquid phase to be monitored which penetrates the sensor 4 via the pipe 10 and leaves it via the pipe 14.

In one particularly advantageous embodiment example of the method of the invention, the oxygen concentration dissolved in running water is continuously doped and the generator 2 is a Faraday cell which, under the effect of the current I which passes through it, provokes electrolysis of the slightly conductive water of the branch circuit connection 5 by producing, in accordance with the Faraday law, a reproduceable quantity of dissolved oxygen at the anode 6 according to the equation:

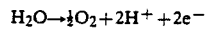

$$H_2O \rightarrow \tfrac{1}{2}O_2 + 2H^+ + 2e^-$$

Figure 3A:
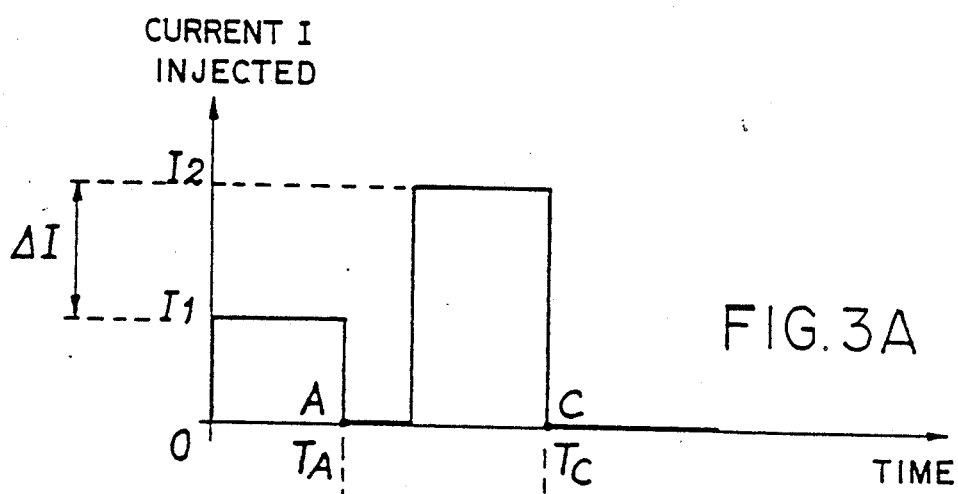
FIGS. 3A and 3B represent the electric intensities respectively passing through the chemical substance generator (FIG. 3A) and the sensor (FIG. 3B) during an automatic calibration cycle of the sensor.
Figure 3B:
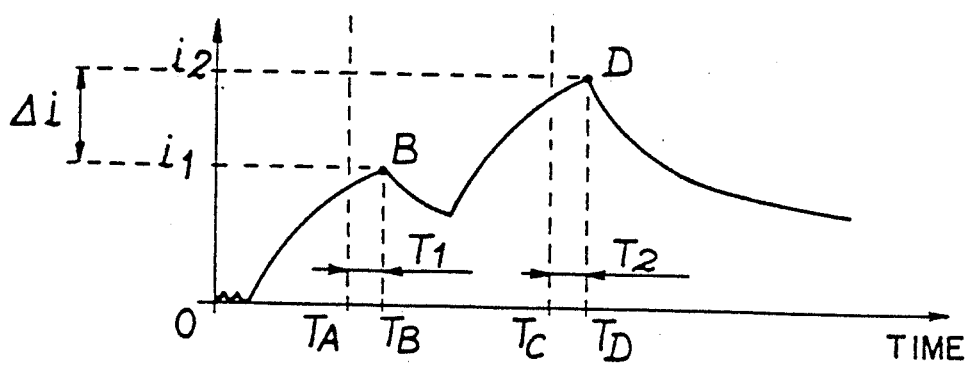

The diagrams of FIGS. 3A and 3B, read concurrently according to the times represented in the abscissae, respectively represent the steps of the current I injected into the generator 2 and for FIG. 3B, the variation of the current i which results from this at the output of the sensor 4.

As can be seen on FIG. 3A, the obtaining of the two successive bursts of the electrochemical substance in question is achieved by injecting into the generator 2 two levels of intensity $I_1$ and $I_2$ separated by a rest period. FIG. 3B shows the consecutive evolution of the current i at the output of the sensor 4, the phase shift between the ascent and descent fronts of the current steps $I_1$ and $I_2$ and the discontinuities of the current i being obviously caused by the hydraulic delay line 3 which introduces a transfer time T between the emission of a burst by the generator 2 and its detection by the sensor 4. By way of experiment, the applicant has established that it was much easier to work on the descent fronts of the injected intensity I and thus on the falling points of the curve i of FIG. 3B so as to accurately reveal this delay. In the two FIGS. 3A and 3B, this delay is measured twice, namely firstly by the difference $T_B - T_A = T_1$ and secondly by the difference $T_D - T_C = T_2$. The values of 1 and $T_2$ are clearly very similar and only differ by virtue of the functioning instabilities of the device, provided the concentration of the substance does not vary in the liquid flow during calibration. In order to work conveniently, the calibration method adopts, as a mean value of the delay time T introduced by the line 3, the mean value $(T_1 + T_2)/2$.

As seen previously, the generator 2 delivers known quantities of the electrochemical substance, said quantities being proportional to the current I, but so as to attain the value of the concentration at the time of measuring, it is essential to know the flow, since the concentration C is equal to the quotient of the mass of the substance delivered by the flow Q of the liquid phase.

According to the invention, this measurement is made via a prior calibration of the device, which makes it possible to plot the linear function of the delay time T measured according to the reciprocal value of the flow $1/Q$ in the branch circuit connection 5. The straight line representing this linear function is visible on FIG. 4. Also, it is possible to see that it does not exactly pass through the origin O of the coordinates, but that its ordinate originally has a value $T_O$. This value corresponds to the time $T_O$ which is necessary for the electrochemical substance to traverse the membrane of the sensor and is consequently independent of the flow itself. In other words, even for a theoretically infinite flow, there already exists a delay time $T_O$. By placing the mean value of the delay T measured according to the curves of FIGS. 3A and 3B, namely the value $(T_1+T_2)/2$ on the straight line of FIG. 4, the value of $1/Q$ is obtained, thus making it possible to know the real flow Q in the branch circuit connection 5. This constitutes one of the main advantages of the invention resulting from a combination of the effects of the double burst of the injected substance and the hydraulic delay line.

Work takes place on the curve of FIG. 3B, that is on the initial decreasing points rather than the increasing points, as the decreasing points are much more defined and easier to mark. This results from the fact this level is no longer interfered with by the background noise inherent in any measurement device since work is carried out on intensities i situated well beyond this background noise.

The electrochemical substance concentrations added by the generator 2 during the injection of the two current levels $I_1$ and $I_2$ are approximately of the same order of magnitude as the concentration C measured and also therefore most often equal so as to interfere as little as possible with the system and to benefit from a return to equilibrium of a reasonable period after a calibration phase. It also ought to be mentioned that there is no point in verifying that the times $T_1$ and $T_2$ are very similar for, if this is not the case, this would signify that this has occured during the calibration cycle in the course of a variation of the concentration C of the electrochemical substance in the basic pipe 1.

Finally, it will be noted that, amongst the advantages of the method of the invention, the measurement method used does not need to determine the zero point of the concentration, since the galvanic sensor 4 only gives any electrons and consequently any current i if said sensor, intended for this purpose, detects the presence of the electrochemical substance.

Figure 4:
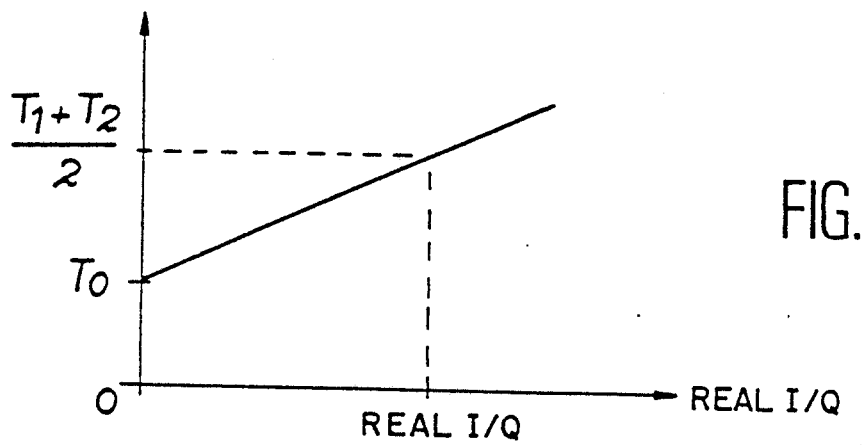
FIG. 4 represents the calibration section of the delay made by the delay line according to the reciprocal value of the flow Q in the pipe, FIG. 5 explains a particular feature of the invention when some oxygen is detected dissolved in the water able to contain an impurity, such as ammonia.

The electrical measurements, previously described with reference to FIGS. 3 and 4, make it possible to determine the actual value K of the meter constant of the sensor 4 at the moment of calibration by determining first of all the additional concentrations $C_1$ and $C_2$ of the electrochemical substances introduced by the generator 2 during the current steps $I_1$ and $I_2$ which are written:

$$C_1 = C_f I_1 / Q,$$

$$C_2 = C_f I_2 / Q,$$

formulae in which $C_f$ is the corrected Faraday constant of the efficiency of electrolysis.

The delay time T introduced by the delay line 3 and selected, as already seen, equal to the mean value:

$$\frac{(T_B - T_A) + (T_D - T_C)}{2}$$

makes it possible to determine the value of the flow Q, since the current actual value of the meter constant K of the sensor 4 by applying the formula is as follows:

$$K = \frac{i_2 - i_1}{C_2 - C_1} = \frac{Q}{C_f} \times \frac{i_2 - i_1}{I_2 - I_1}$$

a formula in which $i_2$ and $i_1$ are the values marked on FIG. 3B of the current i of the sensor 4 at the moment of the points marked B and D visible on FIG. 3B.

In a particularly advantageous example for implementing the method of the invention, said method is used to monitor the oxygen concentration dissolved in water flowing in a pipe. The generator 2 is a Faraday cell which quite simply produces electrolysis of the water and accordingly delivers bursts of oxygen into the branch circuit connection 5 in a quantity proportional to the current I which passes through it, and the sensor 4 is a galvanic cell whose electrodes are respectively made of lead and silver.

Figure 5:
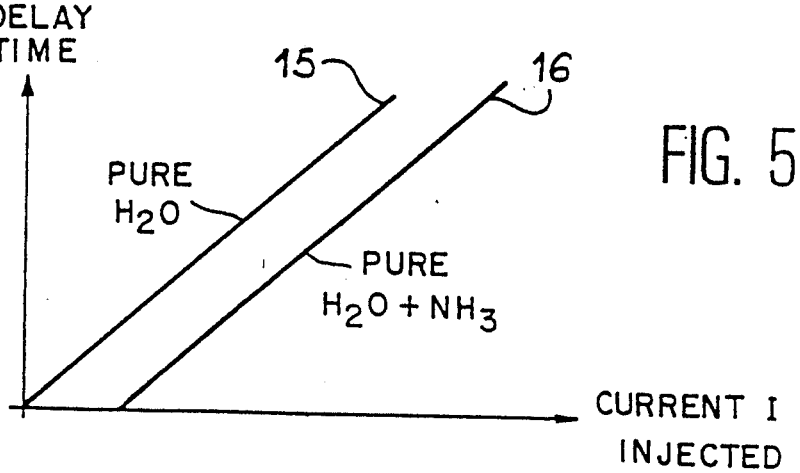

It ought to also be mentioned that the method according to the invention is still applicable, even if this water is not pure and contains, for example, foreign bodies which are split up in the Faraday cell 2 by consuming electrons likely to affect the measurement. In particular, this is the case when this water contains an impurity of dissolved ammonia gas $NH_3$ and, as can be seen from FIG. 5, that the presence of ammonia in the water merely causes the straight line of dissolved oxygen concentration to move parallel to itself according to the injected intensity of 15 and 16 by retaining the same slope. All the above constitutes a significant advantage of the method of the invention.

By way of example of the orders of magnitude, the quantities of oxygen injected by the generator 2 are about one thousandth of the one which would result in saturation of the water circulating in the pipe 1, the calibration of the sensor 4 lasting several minutes and the loss of real time, namely the period during which the sensor 4 is blind to a real high increase at the time of a calibration, not exceeding several tens of seconds.

Of course, the method of the invention may be applied for the dosing of chemical substances other than oxygen, as for example, the dosing of the concentration of chlorides in the water. To this effect, the ions generator $Cl^-$ in the flowing water is an electrolysis cell whose electrodes are respectively made of copper and an Ag-AgCl alloy, and the electrochemical sensor 4 is selected as obviously having a specific electrode of the chlorine ion.

Figure 6:
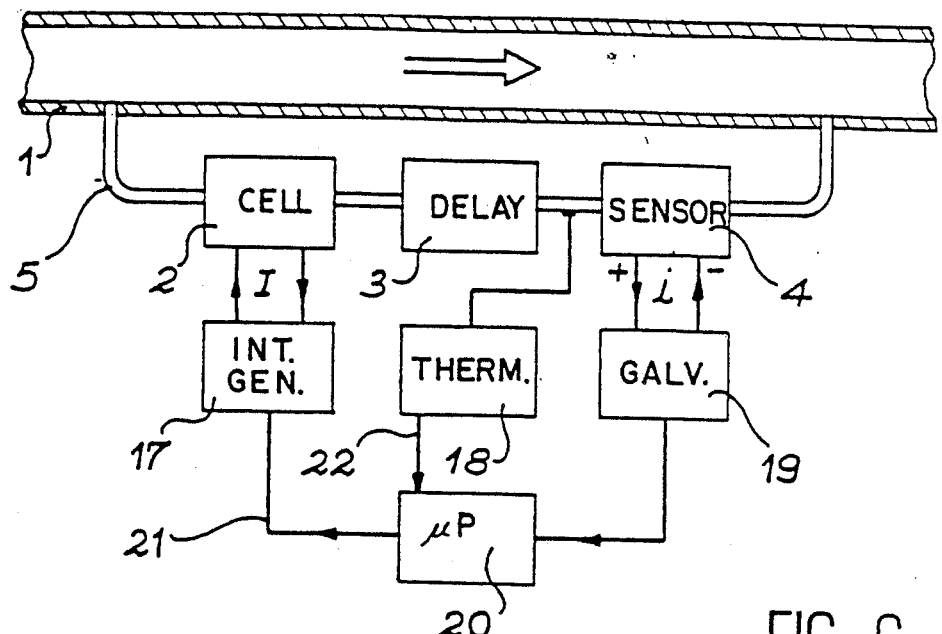
FIG. 6 is a skeleton diagram of the device used to implement the method of the invention when, so as to function automatically, all the sequences required are monitored with the aid of a microprocessor.

Finally, FIG. 6 is a skeleton diagram of an automatic installation able to implement, with the aid of a microprocessor, the calibration method of the invention.

FIG. 6 shows the elements of FIG. 1 having the same reference numbers, as well as an intensity generator 17 generating the current I intended to feed the cell 2, a thermometer 18 continuously monitoring the temperature of the liquid flowing in the branch circuit connection 5 and a galvanometer 19 which measures the value i of the current of the sensor 4. A microprocessor 20 continuously receives indications of the galvanometer 19 and thermometer 18 so as to calculate the value of the concentration of the electrochemical substance monitored by the sensor 4 in the pipe 5; this microprocessor 20 controls at times programmed in advance by the user the intensity generator 17 by means of the line 21 with a view to controlling the Faraday cell 2 and the injection of bursts of electrochemical substances required to start a calibration cycle of the sensor 4. Once the value of the constant K has been calculated from the values $I_1$, $I_2$, $i_1$, $i_2$ and Q, the microprocessor 20 integrates the new value of this constant K so as to carry out continuous monitoring of the concentration detected by the sensor 4.

What is claimed is:

1. A method of automatically calibrating an electrochemical sensor that measures the concentration of a dissolved liquid phase electrochemical substance constituting a liquid flowstream flowing in a pipe, said method including the following steps:

placing on the pipe carrying the liquid flowstream to be monitored upstream of the electrochemical sensor, a generator suitable for injecting into the liquid flowstream standard quantities of the substance whose concentration is desired to be measured;

placing a delay line having a given volume in the same flow path between said generator and the electrochemical sensor;

operating the generator to inject successively into the liquid flowstream two bursts of known quantities of the electrochemical substance corresponding to the concentrations $C_1$ and $C_2$ in the liquid flowstream;

determining from the indications of the electrochemical sensor, the delay T introduced by said delay line for each burst and deducing from the delay times the liquid flow rate Q; and calculating the meter constant K of the sensor for the substance concentration as indicated by the sensor by producing the ratio of the difference of the indications of the sensor to the difference of the concentrations $C_2$-$C_1$.

2. The calibration method according to claim 1, wherein:

the generator is a Faraday cell with two electrodes immersed in the liquid flowstream to be monitored and suitable for freeing in this liquid concentrations of the electrochemical substance with the form $C = C_f I/Q$, $C_f$ being the corrected Faraday constant of electrolysis efficiency, I being the intensity of the current injected into the cell and Q being the liquid flow rate;

the electrochemical sensor for measuring the concentration of the electrochemical substance is a galvanic membrane cell in contact with the liquid to be monitored and has two electrodes immersed in an electrolyte and delivers a current $i = KC$, K being the meter constant of the sensor whose stability is verified, and C being the value of the concentration of the electrochemical substance in the liquid flowstream to be monitored;

the delay T, introduced by the delay line between the time of injecting a substance by the Faraday cell and detection of the substance by the sensor according to the liquid flow rate Q, is experimentally determined, the function $T = f(1/Q)$ being linear by definition;

two levels of currents $I_1$ and $I_2$ are injected successively into the Faraday cell, each said current level freeing in the pipe concentrations $C_1$ and $C_2$ of the electrochemical substance so that $C_1 = C_f I_1/Q$ and $C_2 = C_f I_2/Q$;

from the output of said galvanic membrane cell is determined the electrode current values $i_1$ and $i_2$ corresponding to the respective times $T_B$ and $T_D$ when the electrode current i begins to decrease after the respective stopping times $T_A$ and $T_C$ of said current levels $I_1$ and $I_2$;

the flow rate Q in the pipe is calculated at the time of the experiment by carrying to the linear function $T = f(1/Q)$, the mean value of delay time T:

$$\frac{(T_B - T_A) + (T_D - T_C)}{2} \; ; \text{and}$$

deduced from this is the actual value of the meter constant K of the cell via the formula:

$$K = \frac{Q}{C_f} \times \frac{i_2 - i_1}{I_2 - I_1}.$$

3. The calibration method according to claim 2, wherein the dissolved liquid phase electrochemical substance is a solution of oxygen in water, the Faraday cell is cylindrically-shaped with concentric electrodes made of stainless steel, and the galvanic membrane cell has electrodes made of lead and silver, respectively.

4. The calibration method according to any one of claims 1 to 3, wherein the delay line located between the generator and the sensor is a helicoid-shaped stainless steel tube with an internal volume of about 100 cm$^3$.

5. The calibration method according to claim 1 or 2 wherein said sensor measures the concentration of chlorides in water and has a specific electrode for the measurement of the chlorine concentration, and said generator is an electrolysis cell having electrodes made of Cu and an Ag-AgCl alloy, respectively.

* * * * *